(12) United States Patent
Praharaj et al.

(10) Patent No.: US 11,547,771 B2
(45) Date of Patent: Jan. 10, 2023

(54) SELF-SANITIZING TOUCHSCREEN COVER

(71) Applicant: Xerox Corporation, Norwalk, CT (US)

(72) Inventors: Seemit Praharaj, Webster, NY (US); Douglas K. Herrmann, Webster, NY (US); Chu-Heng Liu, Penfield, NY (US); Paul J. McConville, Webster, NY (US); Jason M. LeFevre, Penfield, NY (US); Linn C. Hoover, Webster, NY (US); David A. VanKouwenberg, Avon, NY (US)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 17/177,300

(22) Filed: Feb. 17, 2021

(65) Prior Publication Data
US 2022/0257810 A1 Aug. 18, 2022

(51) Int. Cl.
*H04N 1/00* (2006.01)
*A61L 2/10* (2006.01)

(52) U.S. Cl.
CPC ............ *A61L 2/10* (2013.01); *H04N 1/00392* (2013.01); *H04N 1/00559* (2013.01); *H04N 1/00909* (2013.01); *A61L 2202/14* (2013.01)

(58) Field of Classification Search
CPC ... A61L 2/10; A61L 2202/14; H04N 1/00392; H04N 1/00559; H04N 1/00909
USPC ................. 358/1.11–1.18; 250/338.1, 214.1; 345/905; 361/727
See application file for complete search history.

(56) References Cited

U.S. PATENT DOCUMENTS

| | | | |
|---|---|---|---|
| 6,003,052 A * | 12/1999 | Yamagata | G06F 1/1626 345/905 |
| 7,424,314 B2 | 9/2008 | Park | |
| 8,597,569 B2 | 12/2013 | Gruen et al. | |
| 8,999,237 B2 | 4/2015 | Tumanov | |
| 9,006,680 B2 | 4/2015 | Bettles et al. | |
| 10,265,540 B2 | 4/2019 | Yehezkel | |
| 10,596,281 B1 | 3/2020 | Tchon et al. | |
| 10,617,774 B2 | 4/2020 | Winslow et al. | |
| 2003/0014927 A1* | 1/2003 | Brooks | E04B 1/34305 52/66 |
| 2004/0246281 A1* | 12/2004 | Vanek | G06F 3/0488 345/905 |

(Continued)

OTHER PUBLICATIONS

U.S. Appl. No. 63/018,500. Title: Ultraviolet Disinfection of Electronic Gaming Devices and Other Gaming Equipment, filed Apr. 30, 2020. Paragraphs [87] and [88], Inventors: Jadeja, Rajendrasinh; Coppola, Roberto; Rodriguez, Frank; Purohit, Nimish; Apple, Sandra. (Year: 2020).*

(Continued)

*Primary Examiner* — Chad Dickerson
(74) *Attorney, Agent, or Firm* — Gibb IP Law Firm, LLC

(57) ABSTRACT

An apparatus includes, among other components, a frame adapted to be connected to the exterior surface of a device that has a touchscreen. A retractable cover is operatively connected to the frame. The size of the retractable cover is equal to at least the size of the touchscreen, and the retractable cover is positioned to extend so as to cover the touchscreen. At least one ultraviolet light is also operatively connected to the frame. The ultraviolet light is positioned to direct ultraviolet lighting toward the touchscreen when the retractable cover extends to cover the touchscreen.

20 Claims, 11 Drawing Sheets

(56) References Cited

U.S. PATENT DOCUMENTS

| | | | |
|---|---|---|---|
| 2015/0182647 A1* | 7/2015 | Ranta | G06F 3/0488 |
| | | | 250/214.1 |
| 2016/0106872 A1 | 4/2016 | Martinez | |
| 2017/0064855 A1* | 3/2017 | Tehranchi | G06F 21/00 |
| 2019/0193536 A1* | 6/2019 | Pompili | B60J 7/141 |
| 2019/0365938 A1 | 12/2019 | Romo et al. | |
| 2021/0338864 A1* | 11/2021 | Urban | G07F 17/3216 |

OTHER PUBLICATIONS

Dutton, Gail, UV-C Light Kills SARS/COV-2, Triggering Novel Lighting Options for Public Spaces, 2020, https://www.biospace.com/article/uv-c-light-kills-sars-cov-2-triggering-novel-lighting-options-for-public-spaces, Accessed on Nov. 11, 2020, pp. 1-4.

\* cited by examiner

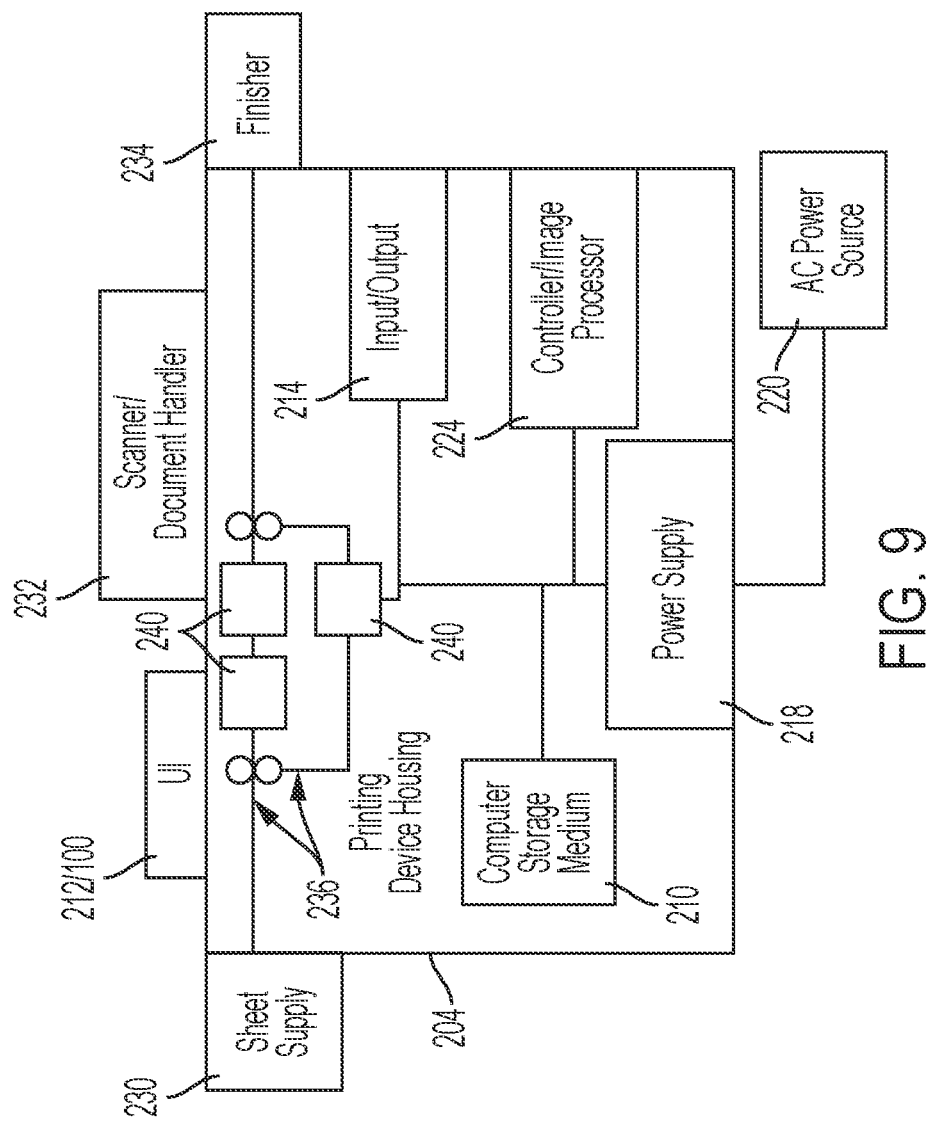

SELF-SANITIZING TOUCHSCREEN COVER

BACKGROUND

Systems and methods herein generally relate to touchscreens and to sanitizing devices for such touchscreens.

The interactive touchscreen interface has been widely used to provide access to information and has applications for communication, commerce, entertainment, or education in various industries (retail, food service, hospitality etc.) to improve customer service and streamline operations. Kiosk devices with touchscreens are typically located in high foot traffic settings such as shops, hotel lobbies, or airports and the touchscreens can potentially act as focal points for virus transmission between successive users.

Current sanitizing techniques primarily operate by having either a user or a dedicated individual manually wipe down the touch areas with disinfecting wipes/disinfectant spray. Alternatively, the user may be asked to sanitize their hands with a sanitizer before accessing the touchscreen. Neither of these solutions are automated, each creates tremendous waste, and both are prone to improper implementation. In addition, any protocol that relies on specific individual action may be quite difficult to implement and enforce consistently.

One area of extensive use of touchscreen interfaces is in office and retail printing solutions. Touchscreens in such devices are expected to be shared between multiple users and present similar challenges to those described above. This issue is especially critical for retail applications where self-serve printing installations (e.g., kiosks) are provided in retail stores.

SUMMARY

In an exemplary embodiment, an apparatus herein includes, among other components, a frame adapted to be connected to the exterior surface of a device that has a touchscreen. A retractable cover is operatively (directly or indirectly) connected to the frame. The size of the retractable cover is equal to at least the size of the touchscreen, and the retractable cover is positioned to extend so as to cover the touchscreen. At least one ultraviolet light is also operatively connected to the frame. The ultraviolet light is positioned to direct ultraviolet lighting toward the touchscreen when the retractable cover extends to cover the touchscreen.

In a more specific example, a printing apparatus herein includes a printing engine operatively connected to a processor, a touchscreen operatively connected to the processor, and a frame connected to the exterior of the printing apparatus. The frame is positioned to cover the touchscreen, and the frame includes an access opening opposite the touchscreen. A retractable cover with a reflective underside is operatively connected to the frame. The size of the retractable cover is equal to at least the size of the access opening, and the retractable cover is positioned to extend to cover the access opening. A motor is connected to the retractable cover and operates to retract and extend the retractable cover.

In one embodiment, the frame can have a rectangular cuboid shape (e.g., 6-sided rectangular box) with an open bottom (missing side, no side, etc.) facing the touchscreen. The side of the rectangular cuboid that is opposite the open bottom has the access opening, which is covered by the retractable cover when the retractable cover extends.

In some embodiments, rails are connected to the frame and the retractable cover. The retractable cover is adapted to slide along such rails when the retractable cover extends to cover the access opening. In other embodiments, telescoping members are connected to the frame and the retractable cover. The retractable cover is adapted to extend to cover the touchscreen when the telescoping members extend.

Also, at least one ultraviolet light is operatively connected to the frame. The ultraviolet light is positioned within the frame in a position to direct ultraviolet lighting toward the touchscreen. The processor is adapted to control the ultraviolet light to illuminate the touchscreen with ultraviolet lighting when the retractable cover covers the access opening in the frame. Further, the processor is adapted to control the ultraviolet light to output the ultraviolet lighting at a controlled power for a controlled period of time sufficient to kill viruses and sanitize the touchscreen.

In some embodiments, the processor is adapted to detect when a user has touched the touchscreen. In response, the processor is adapted to perform a sanitizing cycle by controlling the retractable cover to extend and cover the access opening in the frame and controlling the ultraviolet light to output ultraviolet lighting after a user has touched the touchscreen. For example, the processor can detect if a user has made a menu selection using the touchscreen, which would indicate that a user had physical contact with the touchscreen. In another example, apparatuses herein include a sensor that is operatively connected to the frame and processor, and the sensor is positioned to detect interaction with the touchscreen. The sensor can be a motion sensor, camera, etc., that can detect whether a user physically touches a touchscreen.

These and other features are described in, or are apparent from, the following detailed description.

BRIEF DESCRIPTION OF THE DRAWINGS

Various exemplary systems and methods are described in detail below, with reference to the attached drawing Figs., in which:

FIG. 9 is a conceptual diagram illustrating printing devices herein.

DETAILED DESCRIPTION

As mentioned above, current sanitizing techniques are not automated, create tremendous waste, are prone to improper implementation, and are difficult to implement and enforce. Therefore, the apparatuses herein provide an automated solution that provides continuous protection for the users of the touchscreen interface. Thus, the embodiments herein provide an individualized touchscreen experience so that each customer has a clean disinfected surface available for the operation of a machine.

In one example, multiple ultraviolet lights can be located beneath a reflective retractable shield that covers a touchscreen. In embodiments where the shield is mirrored, the ultraviolet light reflects toward the touchscreen to thoroughly disinfect the touchscreen.

A proximity sensor can trigger the shield to retract and expose the touchscreen as the operator approaches. When the operator is finished using the touchscreen, the shield extends to cover the touchscreen and the ultraviolet lights turn on for a predetermined time interval to sanitize the touchscreen. Specifically, ultraviolet (UV) light has three wavelength categories: UV-A, UV-B, and UV-C. The UV-C light has the short-wavelength and is able to effectively penetrate virus cells and damage the nucleic acid, rendering the cells incapable of reproduction, or making such cells microbiologically inactive.

Upon completion of a sanitization cycle, an indicator can appear to show the operator that it is safe to use the touchscreen. When the apparatus is not in use the retractable shield can remain closed so as to not accumulate any airborne contaminants.

The apparatuses herein increase user confidence because the indicator positively informs the user that the touchscreen has been cleaned and is ready for use. This eliminates wasteful, suboptimal and expensive means of disinfection (wipes or sanitizing chemicals), and eliminates human error associated with manual means of disinfection. Thus, the apparatuses herein protect customer health by providing a clean touchscreen interface for each use. The apparatuses herein also reduce transmission of disease in high traffic environments and provide a competitive advantage to retail copy/print shops.

Figure 1:
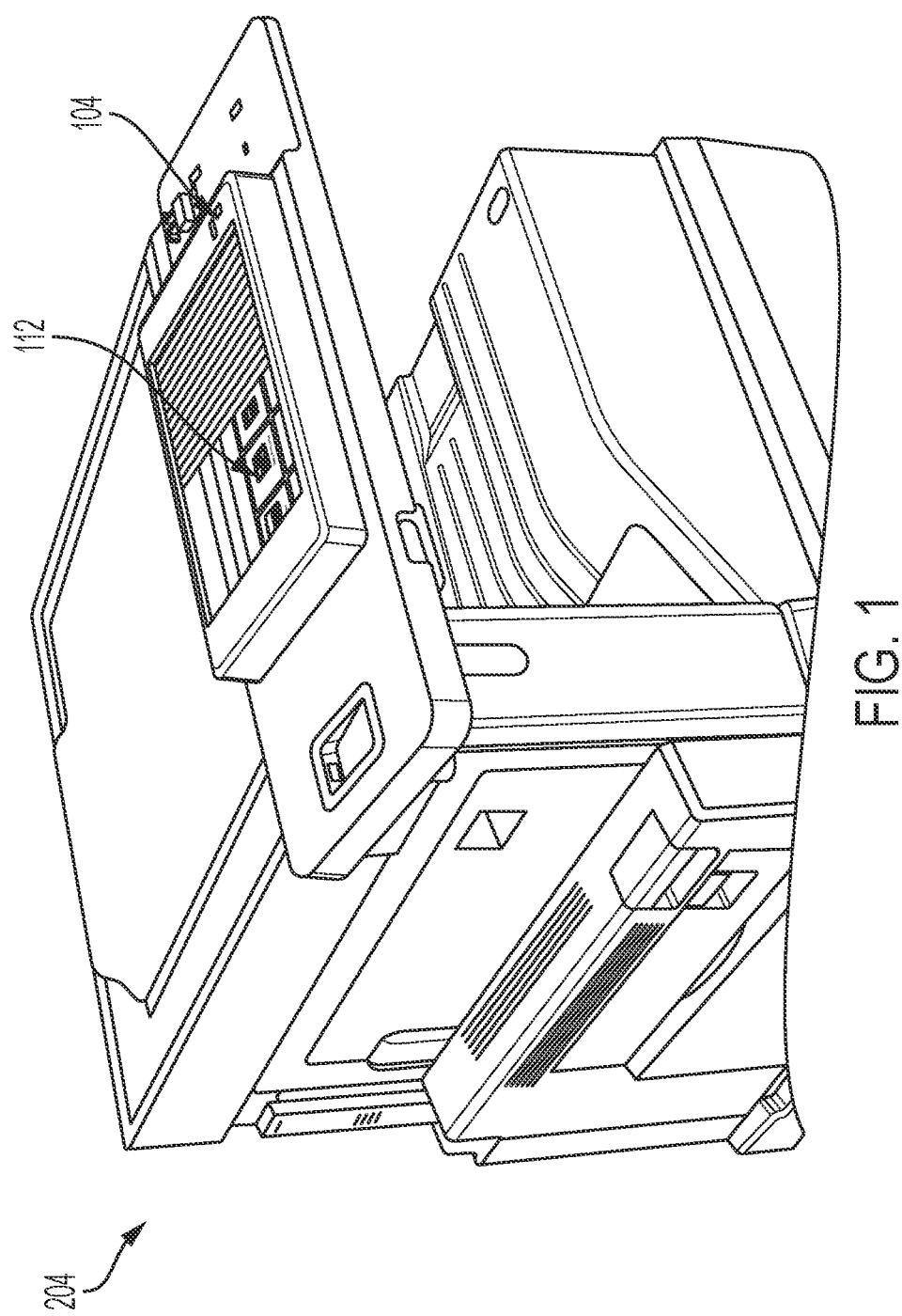
FIGS. 1-2 are schematic perspective-view diagrams illustrating an example of devices herein.
Figure 2:
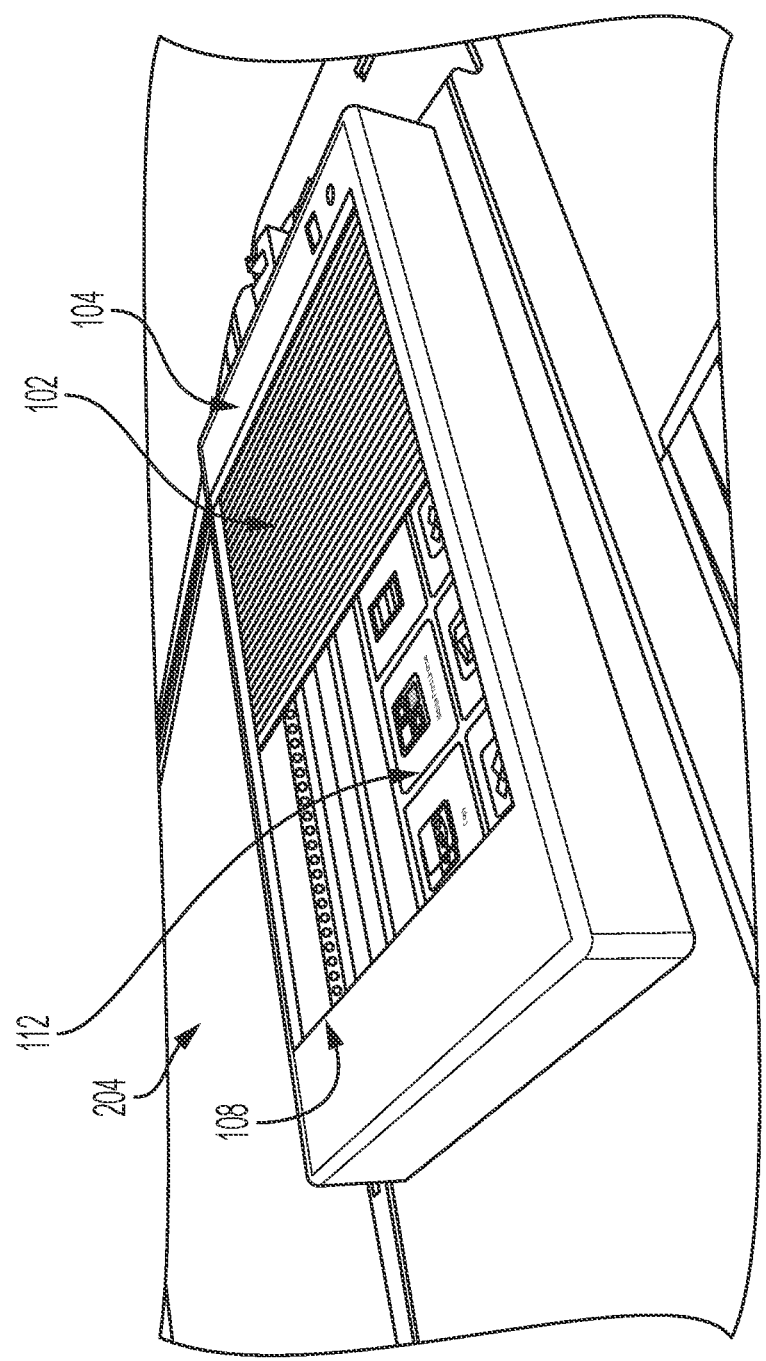
Figure 3:
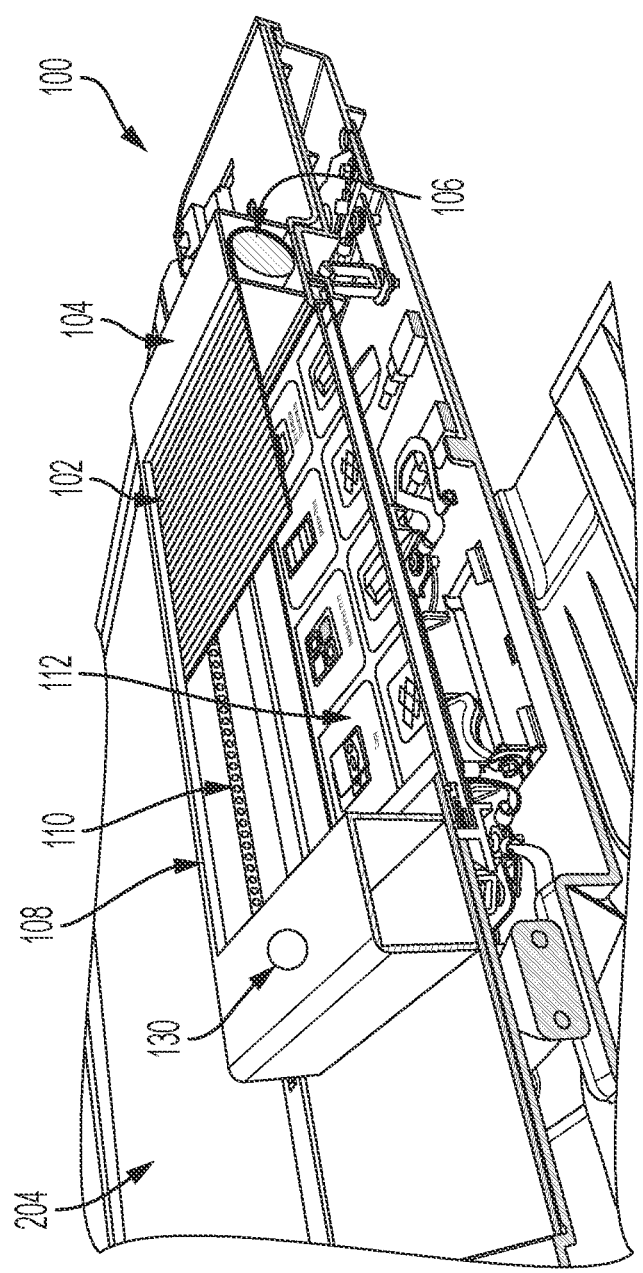
FIG. 3 is a schematic perspective cut-away view diagram illustrating an example of devices herein.

FIGS. 1-3 all show the same device 204 using different perspective views, where FIG. 1 is a full-device perspective view of a printing device 204, FIG. 2 is an expanded perspective view showing only a portion of the printing device 204, and FIG. 3 is a perspective cut-away view, also showing only a portion of the printing device 204. FIGS. 1-3 illustrate that the printing apparatus 204 herein includes (among other components) a touchscreen 112 (that is operatively connected to a processor 224, shown in FIG. 4 that is discussed below) and a frame 104 connected to an exterior of the printing apparatus 204.

The frame 104 is positioned to cover 102 the touchscreen 112, and the frame 104 includes an access opening 108 opposite the touchscreen 112. Therefore, a user reaches through the access opening 108 in the frame 104 to access the touchscreen 112.

A retractable cover 102 is operatively connected to the frame 104. The size of the retractable cover 102 is equal to at least the size of the access opening 108, and the retractable cover 102 is positioned to have the capability to extend to cover the access opening 108. In FIGS. 1-3, the retractable cover 102 is shown extended about ⅓ of the way from one side of the frame 104. A motor 106 is connected to the retractable cover 102 and operates to retract and extend the retractable cover 102.

Also, at least one ultraviolet light 110 is operatively connected to the frame 104. The ultraviolet light 110 is positioned within the frame 104 in a position to direct ultraviolet lighting toward the touchscreen 112. Specifically, FIG. 3 illustrates a strip of ultraviolet light emitting diodes (UV LED) as the ultraviolet light 110, although any ultraviolet light source could be used herein. The processor 224 is adapted to automatically control the ultraviolet light 110 to illuminate the touchscreen 112 with ultraviolet lighting when the retractable cover 102 covers the access opening 108 in the frame 104. Further, the processor 224 is adapted to automatically control the ultraviolet light 110 to output the ultraviolet lighting at a controlled power for a controlled period of time sufficient to kill viruses and sanitize the touchscreen 112. For example, as noted above, short-wavelength UV-C light effectively penetrates virus cells and damages the nucleic acid, rendering the cells incapable of reproduction, or making such cells microbiologically inactive.

For convenience, the combined assembly of retractable cover 102, frame 104, ultraviolet lights 110, and other described components are sometimes referred to herein collectively as a "sanitizing device" 100. The sanitizing device 100 can be an independent assembly that is separate from the printing apparatus 204 to which it can be mounted. This allows the sanitizing device 100 to be retrofitted to existing devices 204 by simple attachment of the sanitizing device 100 to the existing devices 204. Power to the components of the sanitizing device 100 can be supplied through an internal power supply (e.g., battery) that can be, for example, a component of the motor 106, or power can be supplied through simple connection (e.g., USB or direct AC or DC power connection) to the power supply of the existing device 204. Additionally, while a printing device is used as the exemplary "apparatus" 204 in the examples herein, the embodiments herein are not limited to only printing devices but instead the apparatus 204 can be any apparatus that has a touchscreen including computerized portable or stationary devices, kiosks, production machines, etc. In other words, the sanitizing device 100 is a stand-alone device and can be attached to any device having a touchscreen 112.

Optionally, at least the flat side of the retractable cover 102 that faces the touchscreen (arbitrary "bottom" of the retractable cover 102) when the retractable cover 102 is extended can be highly reflective (e.g., having a greater than 90%, 95%, etc., reflectivity). Further, when the retractable cover 102 is extended, the retractable cover 102, the interior of the frame 104, and the top of the touchscreen 112 form a 6-sided light-enclosed box and the reflectivity of the bottom of the retractable cover 102 helps direct all the ultraviolet lighting within this light-enclosed box to the top surface of the touchscreen 112. Thus, the ultraviolet light 110 is positioned within this light-enclosed box to illuminate the inside of the light-enclosed box that is exposed to the top of the touchscreen 112. To further aid in directing all ultraviolet lighting within the light-enclosed box toward the top surface of the touchscreen 112, the interior sides of the frame 104 can also be highly reflective.

FIG. 3 shows an optional indicator 130 (e.g., light, sign, etc.). Upon completion of a sanitization cycle, the indicator 130 can change (e.g., a light can come on, a sign may change, a color may change, etc.) to show the operator that a sanitizing cycle has been performed since the last user touched the touchscreen 112 and that it is now safe to use the touchscreen 112. The apparatuses herein increase user confidence because the indicator 130 positively informs the user that the touchscreen 112 has been cleaned since last use and is now ready for use.

Figure 4:
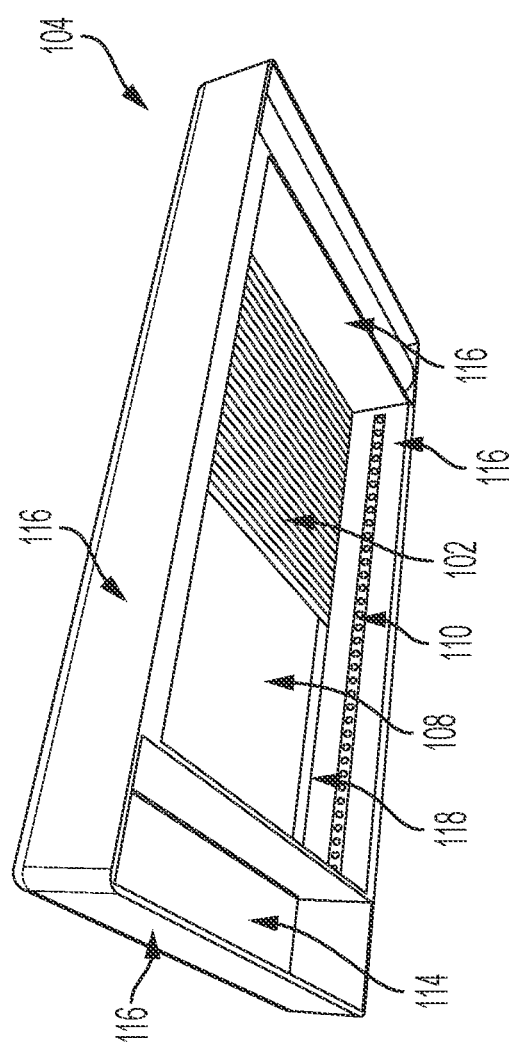
FIG. 4 is a schematic perspective view diagram illustrating an example of a frame herein.

In one embodiment, the frame 104 can have a rectangular cuboid shape (e.g., 6-sided rectangular box) with an open bottom (e.g., missing side, no side, etc.) facing the touchscreen 112. For example, FIG. 4 is a schematic perspective view diagram illustrating an example of the rectangular cuboid frame 104. Conceptually, FIGS. 1-3 show, in perspective view, the rectangular cuboid frame 104 from what can be arbitrarily referred to as the "top," while FIG. 4 relatively illustrates, again in perspective view, the rectangular cuboid frame 104 from what is arbitrarily referred to as the "bottom" (which is opposite the top).

Specifically, FIG. 4 illustrates that the rectangular cuboid frame 104 has four relative "sides" 116 and a relative "top" 114; however, the rectangular cuboid frame 104 does not have (is missing) a relative "bottom" (does not have a $6^{th}$ side). Each of these "sides" 116 and "top" 114 has an outer surface that faces the exterior environment and an opposing inner surface that faces an opposite direction (faces the interior) and which therefore faces the top surface of the touchscreen 112 that makes up part of the 6-sided box and that the frame 104 surrounds and covers. Therefore, the rectangular cuboid frame 104 is a 6-sided rectangular shape that is missing one side (e.g., missing the bottom).

The rectangular cuboid frame 104 is connected to the printing apparatus 204 in a position so that the touchscreen 112 is located where the missing bottom would be located. In this way, the rectangular cuboid frame 104 and the touchscreen 112 combine to form a 6-sided rectangular cuboid box. The access opening 108 is in the top 114 of the rectangular cuboid frame 104 and allows user to reach into the interior of this 6-sided rectangular cuboid box so as to touch the touchscreen 112. Thus, the side or top 114 of the rectangular cuboid 104 that is opposite the open bottom contains the access opening 108, which is covered by the retractable cover 102 when the retractable cover 102 extends.

In some embodiments, rails or guide slots 118 (shown in FIG. 4) are connected to the frame 104 and the retractable cover 102. The retractable cover 102 is adapted to slide along such rails/slots 118 when the retractable cover 102 extends to cover 102 the access opening 108.

Figure 5A:
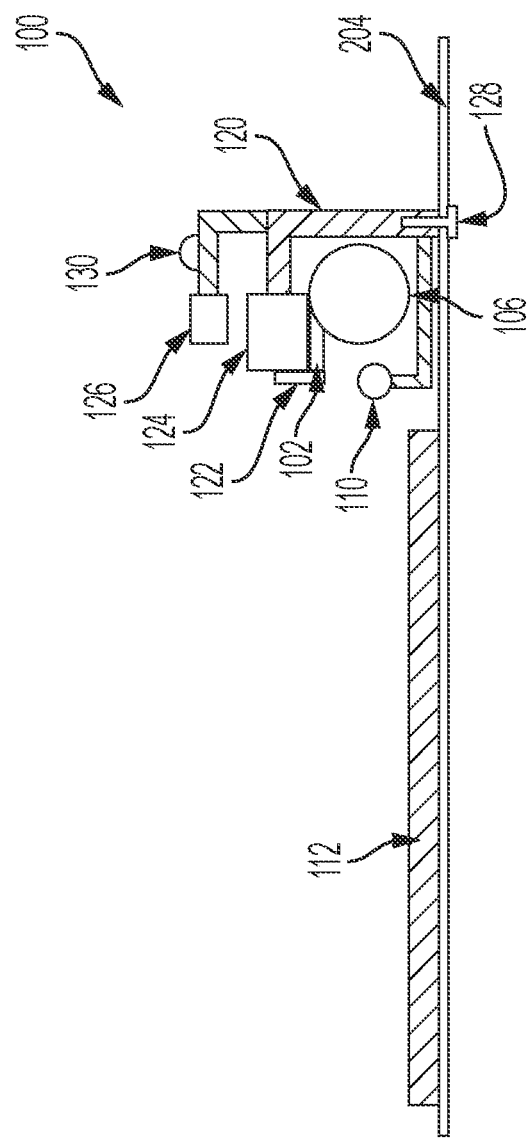
FIGS. 5A-5C are schematic cross-sectional diagrams illustrating an example of device operations herein.
Figure 5B:
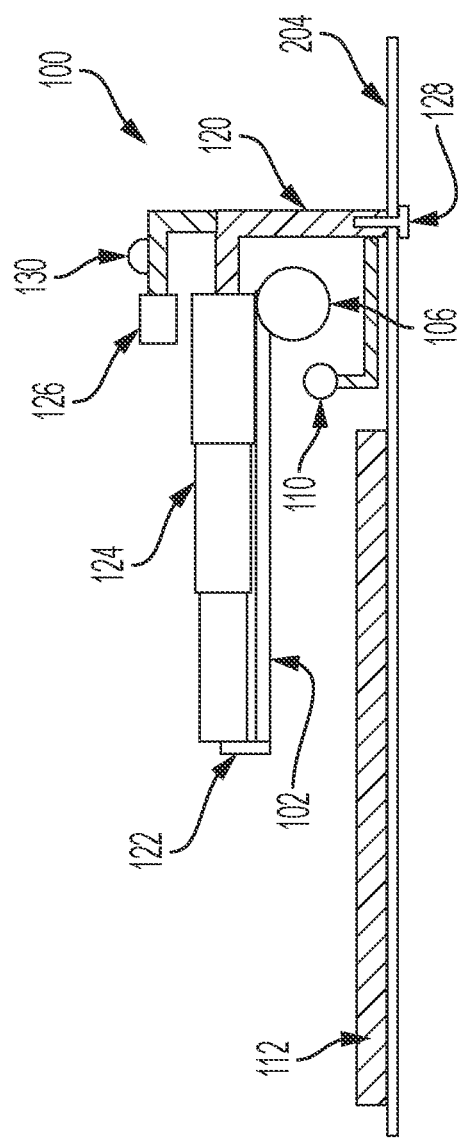
Figure 5C:
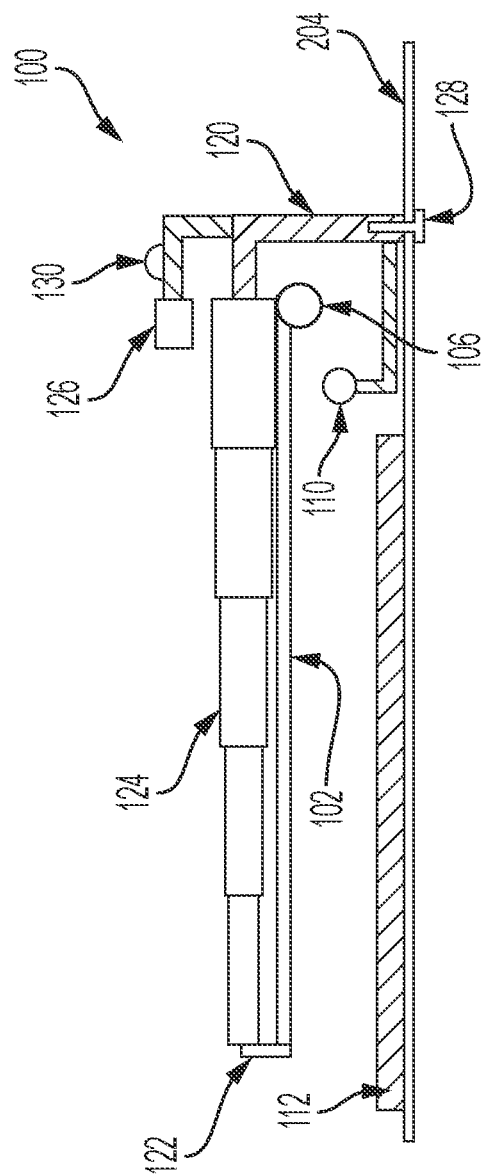

As shown in FIGS. 5A-5C, in other embodiments telescoping members 124 are connected to a different style frame 120 and the retractable cover 102. As shown in FIGS. 5A-5C, the retractable cover 102 is adapted to extend to cover 102 the touchscreen 112 when the telescoping members 124 extend. In greater detail, FIGS. 5A-5C illustrate the frame 120 connected to a surface (e.g., the exterior surface) of the apparatus 204 by any form of connector 128 (screw, bolt, rivet, adhesive, bonding, etc.); or the frame 120 could be an integral part of the apparatus 204.

The frame 120 includes projections, shapes, or components that hold and support the aforementioned cover 102, motor 106, and ultraviolet light 110. Additionally, the frame 120 includes components that hold and support one or more telescoping members 124, a sensor 126, and other possible components. Further, in contrast to the rectangular cuboid frame 104 discussed above, the frame 120 shown in FIGS. 5A-5C does not necessarily surround the touchscreen 112, but instead the frame 120 is adapted to be attached to the exterior surface of the apparatus 204 that is adjacent only one side of the touchscreen 112. This allows the frame 120 and cover 102 to be smaller and more compact overall when compared to previous embodiments. This potentially allows easier access to the touchscreen when the retractable cover 102 is retracted (as shown in FIG. 5A), as the sanitizing device 100 in this embodiment is positioned only adjacent the touchscreen 112 when fully retracted and on only one side of the touchscreen 112 (e.g., not surrounding the touchscreen 112).

Additionally, a connector 122 can connect the distal end of the retractable cover 102 to the telescoping members 124. With this, as the telescoping members 124 extend (as shown in FIGS. 5B and 5C, and this extension can be executed by the motor 106) the retractable cover 102 is pulled out to also be extended (or extension of the retractable cover 102 can pull and extend the telescoping members 124). The telescoping members 124 provide physical support for the extended cover 102 and prevent the retractable cover 102 from drooping when extended, which can avoid the retractable cover 102 making contact with the touchscreen 112.

Even though the sanitizing device 100 is positioned only adjacent the touchscreen 112 in this embodiment, the sanitizing device 100 is in a position to cause the retractable cover 102 to extend fully across the touchscreen 112. Again, the bottom side of the retractable cover 102 can be reflective so that the ultraviolet lighting output by the ultraviolet light 110 is applied mostly to the top surface of the touchscreen 112 (even if some of the ultraviolet lighting is lost along the sides and end of the touchscreen 112.

In some embodiments, the processor 224 is adapted to detect when a user has touched the touchscreen 112. The processor 224 is adapted to control the retractable cover 102 to extend after a user has touched the touchscreen 112. For example, the processor 224 can detect if a user has made a menu selection using the touchscreen 112, which would indicate that a user had physical contact with the touchscreen 112. In another example, apparatuses 100 herein can include the sensor 126 that is operatively connected to the frame 104 and processor 224, and the sensor 126 is positioned to detect interaction with the touchscreen 112. The sensor 126 can be a motion sensor 126, camera, etc., that can detect whether a user physically touches a touchscreen 112 and whether a user is approaching or in front of the apparatus 204.

Thus, the retractable cover 102 can remain extended over the touchscreen 112 until the sensor 126 detects the presence of a user approaching or in front of the apparatus 204. If a user in detected, the retractable cover 102 automatically retracts to allow the user to interact with the touchscreen 112. With other options, the retractable cover 102 may be retracted by default and may only extend during a sanitizing cycle. Either way, after each user has touched the touchscreen 112, a sanitizing cycle is completed. A sanitizing cycle is performed by the retractable cover 102 automatically extending over the touchscreen 112 and the ultraviolet lights 110 automatically outputting ultraviolet lighting for a specified time. Whether the retractable cover 102 remains extended after a sanitizing cycle can be a user selectable option.

Figure 6:
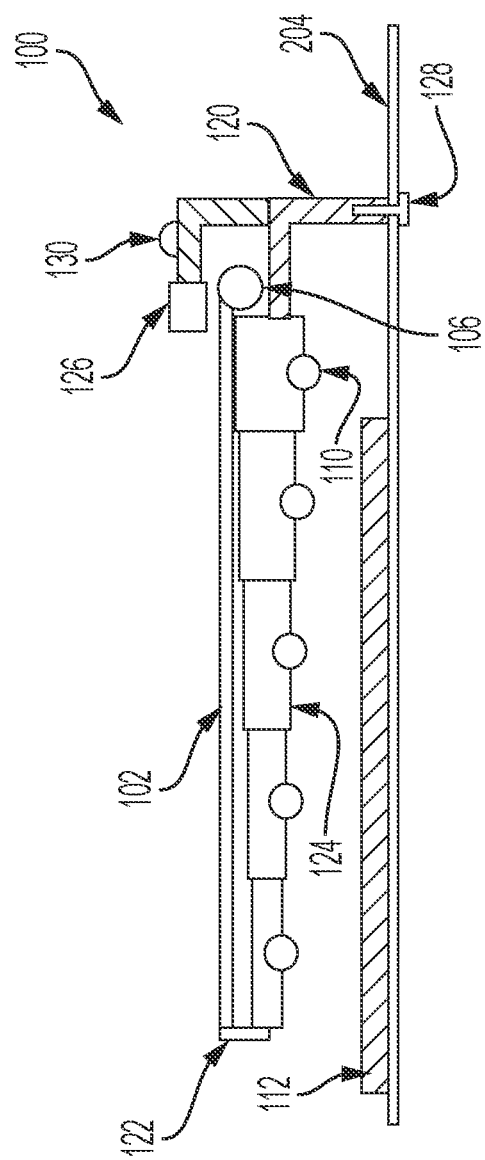
FIGS. 6-8 are schematic cross-sectional diagrams illustrating an example of devices herein.

FIG. 6 illustrates a structure that is similar to that shown in FIGS. 5A-5C; however, in FIG. 6 the telescoping members 124 are positioned below the retractable cover 102. In other words, in the structure in FIG. 6 the telescoping members 124 are positioned between the retractable cover 102 and the touchscreen 112 when the retractable cover 102 is extended. As an option, in the embodiment shown in FIG. 6, the ultraviolet lights 110 can be connected to the telescoping members 124 to allow a more even light distribution.

Figure 7:
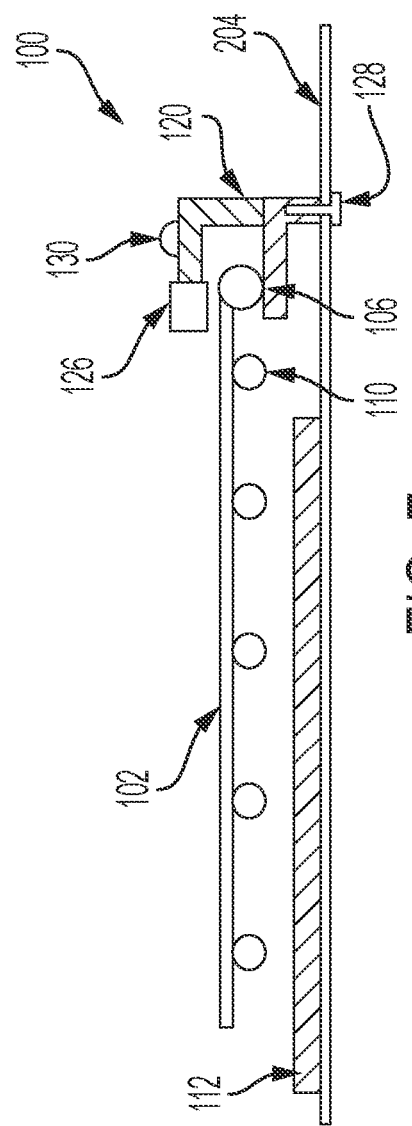

FIG. 7 illustrates a structure similar to that shown in FIG. 6; however, in the structure shown in FIG. 7, the telescoping members 124 are not included and the ultraviolet lights 110 are attached directly to the bottom of the retractable cover 102. In the embodiment shown in FIG. 7, the retractable cover 102 has sufficient structural rigidity to remain self-supported above, and separated from, the touchscreen 112.

Figure 8:
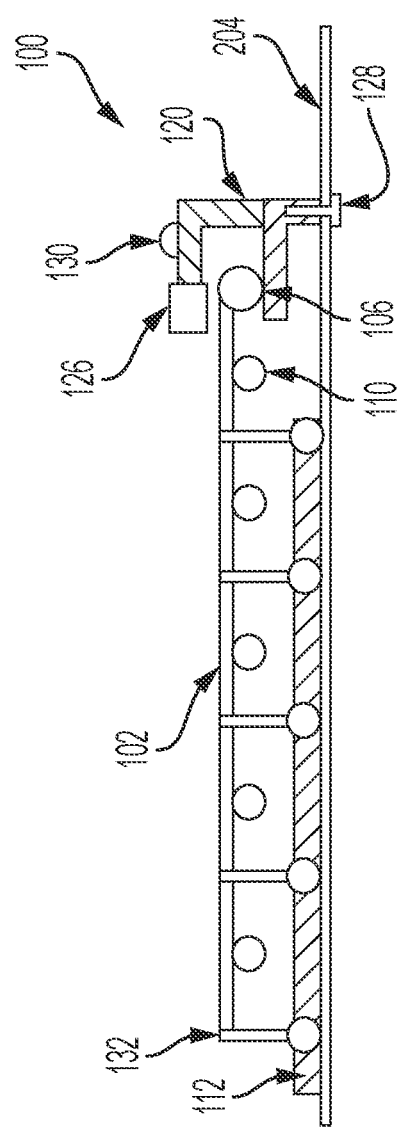

FIG. 8 illustrates a structure similar to that shown in FIG. 7; however, in the structure shown in FIG. 8, wheeled supports 132 are attached to the retractable cover 102. The wheeled supports 132 include a deployable (e.g., rotatable) frame member connecting a support wheel to the retractable cover 102. In some embodiments the wheeled supports 132 are permanently and rigidly fixed at a right angle to the retractable cover 102. In other embodiments the wheeled supports 132 are connected by a locking pin or axle to the retractable cover 102, which allows the wheeled supports 132 to drop down and lock into position to support the retractable cover 102 as the retractable cover 102 extends. The support wheels of the wheeled supports 132 can ride in a dedicated track or can ride on (e.g., directly contact) the exterior of the apparatus 204. In the embodiment shown in FIG. 8, the wheeled supports 132 deploy (e.g., rotate or drop down) to support the retractable cover 102 to keep the retractable cover 102 above, and separated from, the touchscreen 112 in a similar manner to which the telescoping members 124 keep the retractable cover 102 separated from the touchscreen 112.

Therefore, with the structure shown in FIGS. 5A-8, the size of the retractable cover 102 is equal to at least the size of the touchscreen 112, and the retractable cover 102 is positioned to extend so as to cover the touchscreen 112 during a sanitizing cycle. Also, at least one ultraviolet light 110 is operatively connected to the frame 120. The ultraviolet light 110 is positioned to direct ultraviolet lighting toward the touchscreen 112 when the retractable cover 102 extends to cover the touchscreen 112.

These devices eliminate wasteful, suboptimal and expensive means of disinfection (wipes or sanitizing chemicals), and eliminate human error associated with manual means of disinfection. Thus, the sanitizing devices 100 herein protect customer health by providing a clean touchscreen 112 interface for each use. The sanitizing devices 100 herein also reduce transmission of disease in high traffic environments and provide a competitive advantage to retail copy/print shops.

These devices include (among other components) what is generically referred to herein as a "frame" 104/120. The frame 104/120 can comprise many different components of the apparatus, which are elements of the apparatus and which are directly or indirectly connected to each other. Thus, the frame herein can include any or all of the various elements that physically support the enumerated components discussed below. In the attached drawings, identification numeral 104/120 is used to indicate the different items that can be considered this generically defined "frame." All the individual components discussed below are in a fixed location (even though many of the following components move, rotate, etc., in their fixed locations relative to the frame 104/120) and therefore all the following components are directly or indirectly connected to the frame 104/120 in some way.

FIG. 9 illustrates many components of printer structures 204 herein that can comprise, for example, a printer, copier, multi-function machine, multi-function device (MFD), etc. The printing device 204 includes a controller/tangible processor 224 and a communications port (input/output) 214 operatively connected to the tangible processor 224 and to a computerized network external to the printing device 204. Also, the printing device 204 can include at least one accessory functional component, such as a user interface (UI) assembly 212. The user interface assembly 212 includes the touchscreen 112 and sanitizing device 100 discussed above. The user may receive messages, instructions, and menu options from, and enter instructions through, the user interface or control panel 212.

The input/output device 214 is used for communications to and from the printing device 204 and comprises a wired device or wireless device (of any form, whether currently known or developed in the future). The tangible processor 224 controls the various actions of the printing device 204. A non-transitory, tangible, computer storage medium device 210 (which can be optical, magnetic, capacitor based, etc., and is different from a transitory signal) is readable by the tangible processor 224 and stores instructions that the tangible processor 224 executes to allow the computerized device to perform its various functions, such as those described herein. Thus, as shown in FIG. 9, a body housing has one or more functional components that operate on power supplied from an alternating current (AC) source 220 by the power supply 218. The power supply 218 can comprise a common power conversion unit, power storage element (e.g., a battery, etc), etc.

The printing device 204 includes at least one marking device (printing engine(s)) 240 that use marking material, and are operatively connected to a specialized image processor 224 (that is different from a general purpose computer because it is specialized for processing image data), a media path 236 positioned to supply continuous media or sheets of media from a sheet supply 230 to the marking device(s) 240, etc. After receiving various markings from the printing engine(s) 240, the sheets of media can optionally pass to a finisher 234 which can fold, staple, sort, etc., the various printed sheets. Also, the printing device 204 can include at least one accessory functional component (such as a scanner/document handler 232 (automatic document feeder (ADF)), etc.) that also operate on the power supplied from the external power source 220 (through the power supply 218).

The one or more printing engines 240 are intended to illustrate any marking device that applies marking material (toner, inks, plastics, organic material, etc.) to continuous media, sheets of media, fixed platforms, etc., in two- or three-dimensional printing processes, whether currently known or developed in the future. The printing engines 240 can include, for example, devices that use electrostatic toner printers, inkjet printheads, contact printheads, three-dimensional printers, etc. The one or more printing engines 240 can include, for example, devices that use a photoreceptor belt or an intermediate transfer belt or devices that print directly to print media (e.g., inkjet printers, ribbon-based contact printers, etc.).

While some exemplary structures are illustrated in the attached drawings, those ordinarily skilled in the art would understand that the drawings are simplified schematic illustrations and that the claims presented below encompass many more features that are not illustrated (or potentially many less) but that are commonly utilized with such devices and systems. Therefore, Applicants do not intend for the claims presented below to be limited by the attached drawings, but instead the attached drawings are merely provided to illustrate a few ways in which the claimed features can be implemented.

Many computerized devices are discussed above. Computerized devices that include chip-based central processing units (CPU's), input/output devices (including graphic user interfaces (GUI), memories, comparators, tangible processors, etc.) are well-known and readily available devices produced by manufacturers such as Dell Computers, Round Rock Tex., USA and Apple Computer Co., Cupertino Calif., USA. Such computerized devices commonly include input/output devices, power supplies, tangible processors, electronic storage memories, wiring, etc., the details of which are omitted herefrom to allow the reader to focus on the salient aspects of the systems and methods described herein. Similarly, printers, copiers, scanners and other similar peripheral equipment are available from Xerox Corporation, Norwalk, Conn., USA and the details of such devices are not discussed herein for purposes of brevity and reader focus.

The terms printer or printing device as used herein encompasses any apparatus, such as a digital copier, bookmaking machine, facsimile machine, multi-function machine, etc., which performs a print outputting function for any purpose. The details of printers, printing engines, etc., are well-known and are not described in detail herein to keep this disclosure focused on the salient features presented. The systems and methods herein can encompass systems and methods that print in color, monochrome, or handle color or monochrome image data. All foregoing systems and methods are specifically applicable to electrostatographic and/or xerographic machines and/or processes.

In addition, terms such as "right", "left", "vertical", "horizontal", "top", "bottom", "upper", "lower", "under", "below", "underlying", "over", "overlying", "parallel", "perpendicular", etc., used herein are understood to be relative locations as they are oriented and illustrated in the drawings (unless otherwise indicated). Terms such as "touching", "on", "in direct contact", "abutting", "directly adjacent to", etc., mean that at least one element physically contacts another element (without other elements separating the described elements). Further, the terms automated or automatically mean that once a process is started (by a machine or a user), one or more machines perform the process without further input from any user. Additionally, terms such as "adapted to" mean that a device is specifically designed to have specialized internal or external components that automatically perform a specific operation or function at a specific point in the processing described herein, where such specialized components are physically shaped and positioned to perform the specified operation/function at the processing point indicated herein (potentially without any operator input or action). In the drawings herein, the same identification numeral identifies the same or similar item.

It will be appreciated that the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims. Unless specifically defined in a specific claim itself, steps or components of the systems and methods herein cannot be implied or imported from any above example as limitations to any particular order, number, position, size, shape, angle, color, or material.

What is claimed is:

1. An apparatus comprising:
    a frame adapted to be connected to an exterior surface of a device having a touchscreen, wherein the frame includes a shorter side and relatively longer side;
    a retractable cover operatively connected to the frame, wherein the retractable cover has a size equal to at least a size of the touchscreen, and wherein the retractable cover is positioned to extend to cover the touchscreen; and
    an ultraviolet light, operatively connected to the frame, is positioned vertically above the touchscreen and below the cover when extended,
    wherein the ultraviolet light is positioned along the longer side of the frame to direct ultraviolet lighting down toward the touchscreen when the retractable cover extends to cover the touchscreen.

2. The apparatus according to claim 1, further comprising rails connected to the frame and the retractable cover, wherein the retractable cover is adapted to slide along the rails when the retractable cover extends to cover the touchscreen.

3. The apparatus according to claim 1, further comprising at least one of telescoping members and wheeled supports connected to the retractable cover, wherein the telescoping members are adapted to extend and the wheeled supports are adapted to deploy when the retractable cover extends to cover the touchscreen.

4. The apparatus according to claim 1, further comprising a sensor operatively connected to the frame, wherein the sensor is positioned to detect interaction with the touchscreen.

5. The apparatus according to claim 1, wherein the frame comprises a rectangular cuboid with an open bottom facing the touchscreen, wherein a side of the rectangular cuboid opposite the open bottom includes an access opening that is covered by the retractable cover when the retractable cover extends to cover the touchscreen.

6. The apparatus according to claim 1, further comprising a motor connected to the retractable cover.

7. The apparatus according to claim 1, wherein the ultraviolet light outputs ultraviolet lighting at a controlled power for a controlled period of time.

8. An apparatus comprising:
    a processor;
    a touchscreen operatively connected to the processor;
    a frame connected to an exterior of the apparatus, wherein the frame is positioned to cover the touchscreen, and wherein the frame includes an access opening opposite the touchscreen, and wherein the frame includes a shorter side and relatively longer side;
    a retractable cover operatively connected to the frame, wherein the retractable cover has a size equal to at least a size of the access opening, and wherein the retractable cover is positioned to extend to cover the access opening; and
    an ultraviolet light, operatively connected to the frame, is positioned vertically above the touchscreen and below the cover when extended,
    wherein the ultraviolet light is along the longer side of the frame in a position to direct ultraviolet lighting down toward the touchscreen, and
    wherein the processor is adapted to control the ultraviolet light to illuminate the touchscreen with ultraviolet lighting when the retractable cover covers the access opening in the frame.

9. The apparatus according to claim 8, further comprising rails connected to the frame and the retractable cover, wherein the retractable cover is adapted to slide along the rails when the retractable cover extends to cover the access opening.

10. The apparatus according to claim 8, further comprising at least one of telescoping members and wheeled supports connected to the retractable cover, wherein the telescoping members are adapted to extend and the wheeled supports are adapted to deploy when the retractable cover extends to cover the touchscreen.

11. The apparatus according to claim 8, further comprising a sensor operatively connected to the frame, wherein the sensor is positioned to detect interaction with the touchscreen.

12. The apparatus according to claim 8, wherein the frame comprises a rectangular cuboid with an open bottom facing the touchscreen, wherein a side of the rectangular cuboid opposite the open bottom includes an access opening that is covered by the retractable cover when the retractable cover extends to cover the access opening.

13. The apparatus according to claim 8, further comprising a motor connected to the retractable cover.

14. The apparatus according to claim 8, wherein the ultraviolet light outputs ultraviolet lighting at a controlled power for a controlled period of time.

15. A printing apparatus comprising:
   a processor;
   a printing engine operatively connected to the processor;
   a touchscreen operatively connected to the processor;
   a frame connected to an exterior of the printing apparatus, wherein the frame is positioned to cover the touchscreen, wherein the frame includes an access opening opposite the touchscreen, and wherein the frame includes a shorter side and relatively longer side;
   a retractable cover operatively connected to the frame, wherein the retractable cover has a size equal to at least a size of the access opening, and wherein the retractable cover is positioned to extend to cover the access opening; and
   an ultraviolet light, operatively connected to the frame, is positioned vertically above the touchscreen and below the cover when extended,
   wherein the ultraviolet light is positioned within the frame along the longer side of the frame in a position to direct ultraviolet lighting down toward the touchscreen,
   wherein the processor is adapted to detect when a user has touched the touchscreen,
   wherein the processor is adapted to control the retractable cover to extend and cover the access opening in the frame after a user has touched the touchscreen, and
   wherein the processor is adapted to control the ultraviolet light to illuminate the touchscreen with ultraviolet lighting when the retractable cover covers the access opening in the frame.

16. The printing apparatus according to claim 15, further comprising rails connected to the frame and the retractable cover, wherein the retractable cover is adapted to slide along the rails when the retractable cover extends to cover the access opening.

17. The printing apparatus according to claim 15, further comprising at least one of telescoping members and wheeled supports connected to the retractable cover, wherein the telescoping members are adapted to extend and the wheeled supports are adapted to deploy when the retractable cover extends to cover the touchscreen.

18. The printing apparatus according to claim 15, further comprising a sensor operatively connected to the frame, wherein the sensor is positioned to detect interaction with the touchscreen.

19. The printing apparatus according to claim 15, wherein the frame comprises a rectangular cuboid with an open bottom facing the touchscreen, wherein a side of the rectangular cuboid opposite the open bottom includes an access opening that is covered by the retractable cover when the retractable cover extends to cover the access opening.

20. The printing apparatus according to claim 15, further comprising a motor connected to the retractable cover.

* * * * *